United States Patent
Castan et al.

(10) Patent No.: US 11,052,165 B2
(45) Date of Patent: Jul. 6, 2021

(54) METHOD FOR VIRUS CLEARANCE

(71) Applicant: Global Life Sciences Solutions USA LLC, Marlborough, MA (US)

(72) Inventors: Andreas Castan, Uppsala (SE); Colin R. Tuohey, Marlborough, MA (US)

(73) Assignee: Global Life Sciences Solutions USA LLC, Marlborough, MA (US)

( * ) Notice: Subject to any disclaimer, the term of this patent is extended or adjusted under 35 U.S.C. 154(b) by 261 days.

(21) Appl. No.: 15/718,831

(22) Filed: Sep. 28, 2017

(65) Prior Publication Data

US 2018/0015189 A1 Jan. 18, 2018

Related U.S. Application Data

(63) Continuation-in-part of application No. 15/561,826, filed as application No. PCT/EP2016/057971 on Apr. 12, 2016.

(60) Provisional application No. 62/149,813, filed on Apr. 20, 2015.

(51) Int. Cl.
*A61L 2/00* (2006.01)
*C12N 5/00* (2006.01)
*C12N 13/00* (2006.01)

(52) U.S. Cl.
CPC ............. *A61L 2/0017* (2013.01); *A61L 2/007* (2013.01); *A61L 2/0023* (2013.01); *A61L 2/0035* (2013.01); *C12N 5/0018* (2013.01); *C12N 13/00* (2013.01); *C12N 2500/32* (2013.01); *C12N 2500/34* (2013.01); *C12N 2500/38* (2013.01); *C12N 2523/00* (2013.01)

(58) Field of Classification Search
CPC .... A61L 2/0017; A61L 2/0023; A61L 2/0035; A61L 2/007; C12N 2523/00; C12N 13/00; C12N 2500/32; C12N 2500/34; C12N 5/0018; C12N 2500/38
See application file for complete search history.

(56) References Cited

U.S. PATENT DOCUMENTS

| | | | |
|---|---|---|---|
| 5,965,086 A | 10/1999 | Rose et al. | |
| 7,420,183 B2 | 9/2008 | Kaiser et al. | |
| 7,629,167 B2 | 12/2009 | Hodge et al. | |
| 2003/0036638 A1* | 2/2003 | Joergensen et al. | 530/387.1 |
| 2004/0062140 A1 | 4/2004 | Cadogan et al. | |
| 2006/0065276 A1* | 3/2006 | Kammer et al. | 128/849 |
| 2010/0075405 A1 | 3/2010 | Broadley et al. | |
| 2010/0317102 A1 | 12/2010 | Suzuki et al. | |
| 2012/0214204 A1* | 8/2012 | Hart et al. | 435/70.3 |
| 2013/0197437 A1 | 8/2013 | Faries et al. | |
| 2014/0293734 A1 | 10/2014 | Kauling et al. | |
| 2015/0218501 A1 | 8/2015 | Kauling et al. | |

FOREIGN PATENT DOCUMENTS

| | | |
|---|---|---|
| AU | A-38767/93 | 2/1993 |
| CA | 2 096 888 C | 4/2004 |
| CN | 2540980 Y | 3/2003 |
| CN | 1569031 A | 1/2005 |

OTHER PUBLICATIONS

Pohlscheidt M. et al., "Implementing high-temperature short-time media treatment in commercial-scale cell culture manufacturing processes", Appl. Microbiol. Biotechnol., 2014, vol. 98, pp. 2965-2971. (Year: 2014).*
Bragt J. V. et al. "Effects of Sterilization on Components in Nutrient Media", Papers presented at a symposium organized by the Department of Horticulture, Agricultural University, Wageningen, The Netherlands on Mar. 4, 1970, published as "Miscellaneous Papers 9 (1971)", total pp. 1-151. (Year: 1971).*
Liu S. et al., "Development and Qualification of a Novel Virus Removal Filter for Cell Culture Applications", Biotechnol. Prog., (2000), vol. 16, pp. 425-434. (Year: 2000).*
Wolff M. W. et al., "Downstream processing of cell culture-derived virus particles", Expert Review Vaccines, 2011, vol. 10, No. 10, pp. 1451-1475. (Year: 2011).*
PCT International Search Report and Written Opinion for PCT Application No. PCT/EP2016/057971 dated Jun. 10, 2016 (9 pages).
Non-Final Office Action for U.S. Appl. No. 15/561,826 dated Jan. 9, 2020 (12 pages).
Japanese Office Action for JP Application No. 2017-554814 dated Nov. 26, 2019 (7 pages).
European Office Action for EP Application No. 16715560.5 dated Sep. 24, 2020 (4 pages).
Chinese Office Action for CN Application No. 2016800227826 dated Sep. 7, 2020 (26 pages with English translation).

* cited by examiner

*Primary Examiner* — Satyendra K Singh
(74) *Attorney, Agent, or Firm* — Eversheds Sutherland (US) LLP

(57) ABSTRACT

The invention discloses a method for virus clearance of a cell culture medium, comprising the steps of: i) providing a bulk medium portion, comprising amino acids and glucose, and a first additive portion, comprising vitamins in aqueous solution; ii) subjecting the bulk medium portion to a high temperature short time treatment (HTST); iii) passing the first additive portion through a virus retentive filter or an ultrafilter; and iv) after steps ii) and iii), mixing the bulk medium portion with the first additive portion to obtain a cell culture medium.

20 Claims, 3 Drawing Sheets

METHOD FOR VIRUS CLEARANCE

CROSS REFERENCE TO RELATED APPLICATIONS

This application is a continuation-in-part of U.S. application Ser. No. 15/561,826 filed on Sep. 26, 2017 which claims the priority benefit of PCT/EP2016/057971 filed on Apr. 12, 2016 which claims priority benefit of U.S. Provisional Application No. 62/149,813 filed Apr. 20, 2015. The entire contents of which are hereby incorporated by reference herein.

TECHNICAL FIELD OF THE INVENTION

The present invention relates to cell culture media and in particular to methods for virus clearance and virus inactivation in cell culture media. The invention also relates to methods of cell cultivation.

BACKGROUND OF THE INVENTION

Cultivation of cells is routinely used for the manufacturing of biopharmaceuticals such as recombinant proteins, antibodies, vaccines etc. The cells are cultivated in bioreactors containing cell culture media, which are complex formulations of cell nutrients and various additives. One issue is that contamination of the cell culture media with viruses may give rise to viral contamination of the biopharmaceutical produced. This is particularly the case when mammalian cells are used and the viruses are mammalian viruses. When microbial cells are used, there is also a risk that bacteriophage virus contaminants in the cell culture medium can attack the microbial cells and negatively affect the product expression.

Cell culture media are normally sterile filtered to remove microbial contaminants, but sterile filters do not remove the small virus particles. Heat treatment can be used to inactivate viruses (see e.g. U.S. Pat. No. 9,493,744, hereby incorporated by reference in its entirety), but certain components in cell culture media are heat sensitive and may be degraded by the heating.

Accordingly, there is a need for elimination of virus contamination in cell culture media without negative effects on the media components.

SUMMARY OF THE INVENTION

One aspect of the invention is to provide a method of clearing and/or inactivating viruses in cell culture media without impairing the suitability of the media for cell culture. This is achieved by a method comprising the steps of:
  i) providing either
    a) a bulk medium portion, comprising amino acids and glucose or
    b) a separate amino acid portion, comprising amino acids and a separate sugar portion, comprising glucose;
  ii) providing a first additive portion, comprising vitamins in aqueous solution;
  iii) subjecting the bulk medium portion or the amino acid and sugar portions to a high temperature short time treatment (HTST);
  iv) passing the first additive portion through a virus retentive filter or an ultrafilter; and
  v) after steps iii) and iv), mixing the bulk medium portion or the amino acid and sugar portions with the first additive portion to obtain a cell culture medium.

One advantage is that the heat sensitive components such as vitamins can be cleared from viruses without heating. A further advantage is that only a small portion of the media needs to be passed through the virus retentive filter/ultrafilter, which has a limited flux performance.

A second aspect of the invention is a method of cultivating cells under essentially virus free conditions. This is achieved by a method comprising the steps of:
  providing a cell culture medium by the method disclosed above;
  transferring the cell culture medium to a bioreactor;
  transferring cells to the bioreactor; and
  cultivating the cells in the cell culture medium in the bioreactor.

Further suitable embodiments of the invention are described in the dependent claims.

DETAILED DESCRIPTION OF THE INVENTION

Definitions

Figure 1:
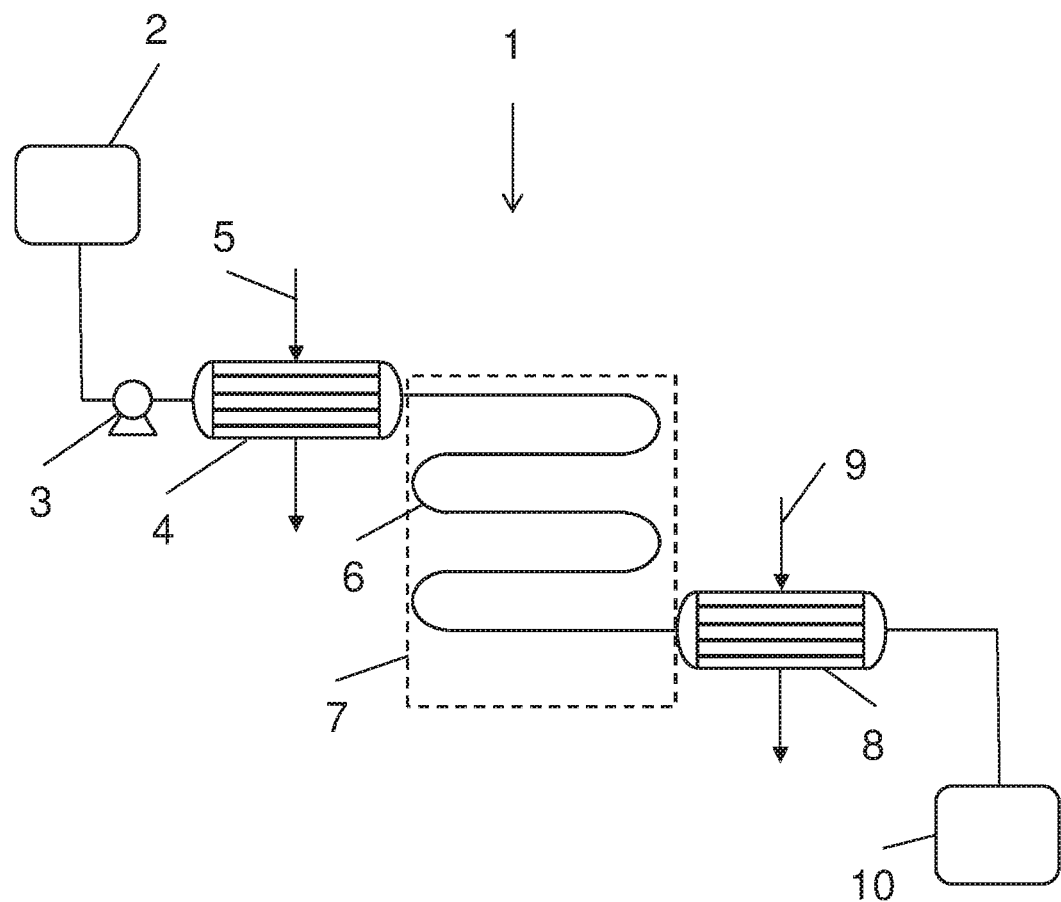
FIG. 1 shows an apparatus for high temperature short time treatment (HTST) according to the invention.
Figure 2:
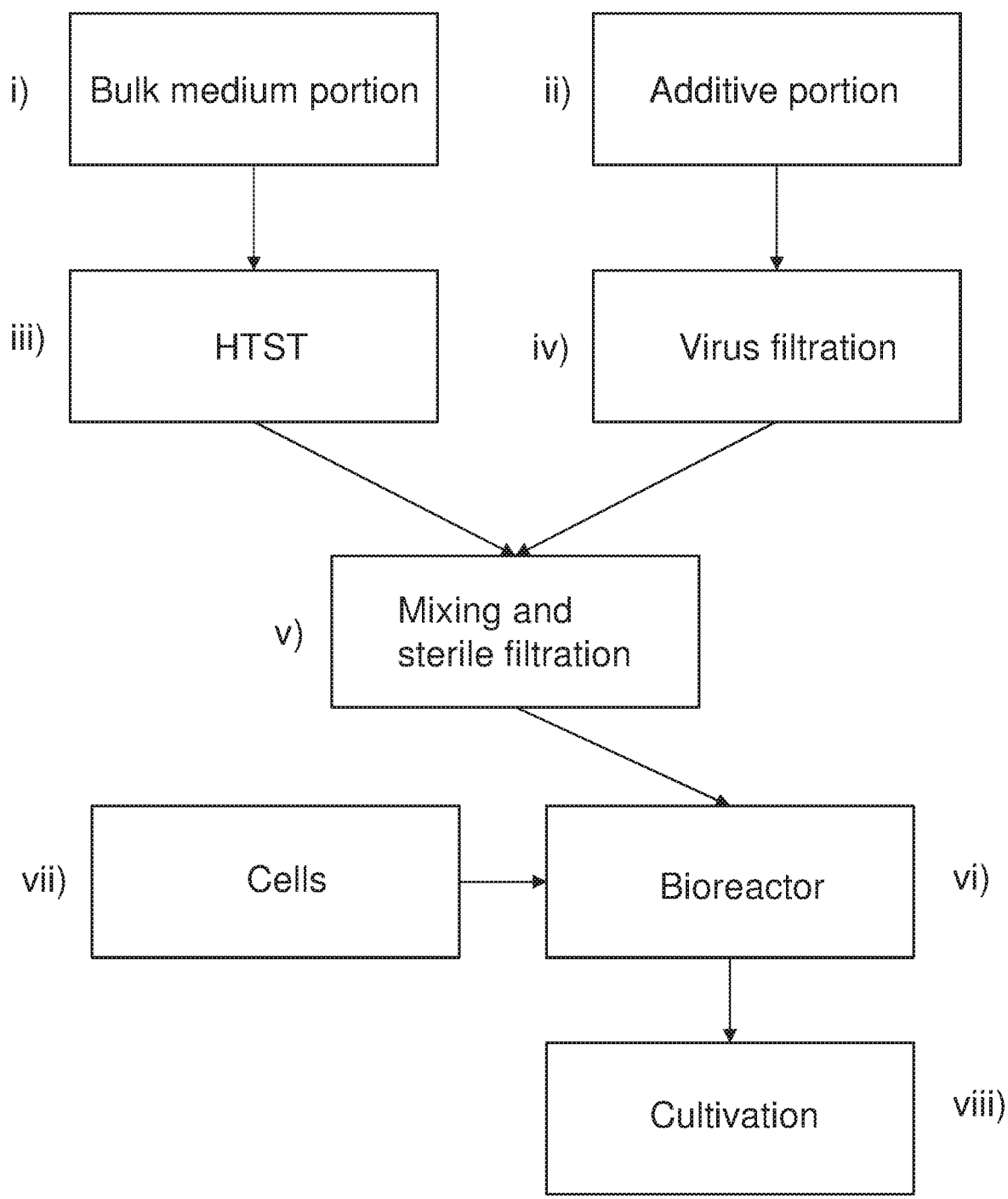
FIG. 2 shows a flow diagram of a method according to the invention.
Figure 3:
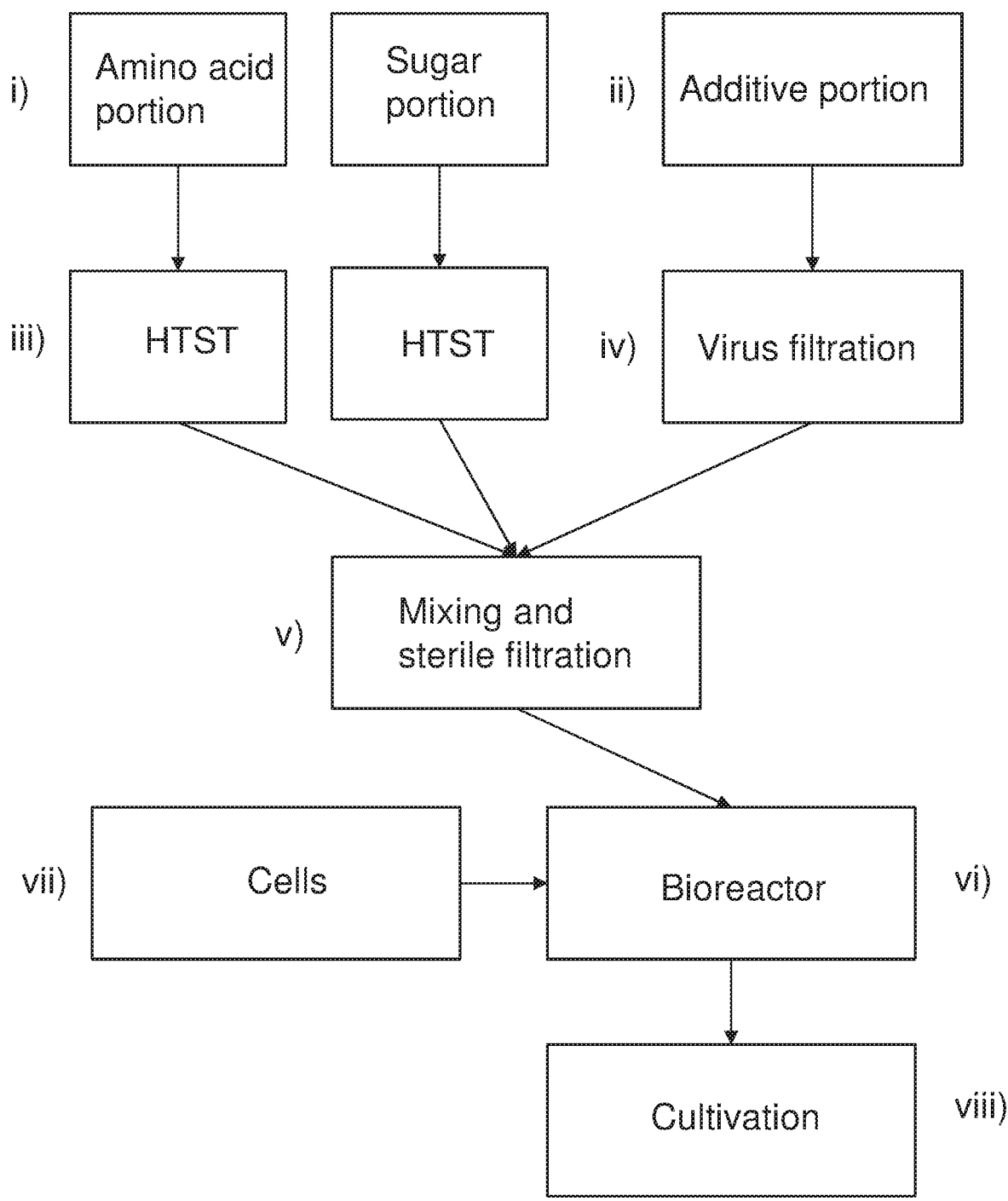
FIG. 3 shows shows a flow diagram of a method according to the invention.

To more clearly and concisely describe and point out the subject matter of the claimed invention, the following definitions are provided for specific terms that are used in the following description and the claims appended hereto.

The singular forms "a" "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least each numerical parameter should at least be construed in light of the number of reported significant digits and by applying ordinary rounding techniques.

As used herein to describe the present invention, directional terms such as "up", down", "upwards", "downwards", "top", "bottom", "vertical", "horizontal", "above", "below" as well as any other directional terms, refer to those directions in the appended drawings.

In one aspect, the present invention discloses a method for virus clearance of a cell culture medium. The method comprises the steps of:

i) Providing a bulk medium portion, comprising amino acids and glucose. In addition to amino acids and glucose, the bulk medium portion may comprise any other non heat-sensitive components of the cell culture medium, including water and buffers. Alternatively, a separate amino acid portion, comprising amino acids, and a separate sugar portion, comprising glucose may be provided. These are provided as aqueous solutions, optionally comprising other non heat-sensitive components such as buffers, salts etc.

ii) Providing a first additive portion, comprising vitamins in aqueous solution. The first additive portion may comprise heat-sensitive vitamins such as thiamine and/or pantothenic acid but it can also comprise other heat-sensitive components, e.g. other vitamins, antibiotics, lipids, nucleotides, growth factors, polyamines, antioxidants etc, along with further minor components of the cell culture medium. The components can suitably have a low molecular weight (e.g. with a molecular weight of <25 kDa). Suitably the first additive portion is a clear and homogeneous solution, such that it easily passes through a virus-retentive filter or an ultrafilter without blocking the filter. It is advantageous if it does not contain species of high molecular weight or species that may combine to form colloids or other precipitates. The volume ratio of the first additive portion to the bulk medium portion may be less than 1:10, such as less than 1:20 or less than 1:50.

iii) Subjecting the bulk medium portion or the amino acid and sugar portions to a high temperature short time treatment (HTST). The HTST may e.g. comprise heating the portion, typically from room temperature (20-25° C.), to a temperature of about 85-110° C., such as 90-105° C. or 93-100° C., maintaining this temperature for about 1 s to about 10 min, such as 5 s-10 min, 5 s-30 s or 10 s-5 min, and cooling the portion to <45° C., such as 1-40° C. or 1-37° C. The rate of heating may suitably be at least 5° C. per s, such as 5-20° C. per s. This can be achieved with a flow-through heater with a high power to liquid volume ratio. The flow-through heater can be a heat exchanger (e.g. a tubular or a plate heat exchanger, heated with hot liquid or steam) or an electric heater, but also e.g. an inductive heater as described in co-pending application PCT EP2016/057971, hereby incorporated by reference in its entirety. The maintaining of the high temperature can be done in a length of tubing (holding circuit) having length and diameter to give the desired hold time at a given liquid flow rate, or alternatively in a hold tank. The cooling can then suitably be done at a rate of at least 5° C. per s, such as 5-20° C. per s. This can be achieved with a flow-through cooler with a high power to liquid volume ratio, e.g. a heat exchanger (cooled with e.g. cold liquid). FIG. 1 shows an exemplary apparatus 1 for carrying out the HTST. The liquid medium portion is conveyed from a first vessel 2 by a pump 3 through a heat exchanger 4 where it is heated with steam or hot liquid 5 to the desired temperature. It then passes through a holding circuit 6, which is thermostated to the treatment temperature and enclosed in insulation 7. The medium portion then passes through a second heat exchanger 8, which is cooled with cold liquid 9, and into a second vessel 10. The temperature at the inlets and outlets of each heat exchanger and in the holding circuit can suitably be measured by temperature sensors (not shown) and regulated by a control unit (not shown) to be within predetermined temperature intervals, ensuring virus inactivation but avoiding overheating of the medium.

iv) Passing the first additive portion through a virus retentive filter or an ultrafilter. Virus retentive filters are commonly used for viral clearance of biopharmaceuticals and are commercially available from several suppliers. Examples include Planova™ 15N, 20N and 35N (Asahi Kasei Bioprocess, Japan), Viresolve™ Pro Shield and Shield H (EMD Millipore, USA), Pegasus™ Prime, Pegasus SV4 and Ultipor™ UDV20 (Pall Biopharmaceuticals, USA) and Virosart™ (Sartorius Stedim Biotech GmbH, Germany). These filters can be used in normal flow filtration mode, i.e. the first additive portion is pumped or otherwise forced (e.g. by gas pressure) through a filter cartridge and the filtered liquid is recovered at an outlet of the cartridge. Alternatively, it is possible to use an ultrafilter—a membrane that only allows molecules below a particular molecular weight cut-off to pass. To ensure that no virus particles can pass the membrane, ultrafilters with Mw cut-off values below 100 kDa, such as below 50 kDa can be most suitable. Such membranes are available e.g. from GE Healthcare Life Sciences, USA, in the form of hollow fiber cartridges. Ultrafiltration membranes should be used under tangential flow filtration conditions, where the first additive portion is pumped through a retentate loop on one side of the filter to generate a permeate on the other side of the filter, which is collected.

v) After steps iii) and iv), mixing the bulk medium portion with the first additive portion to obtain a cell culture medium. If an amino acid and a sugar portion have been HTST-treated separately, they will both be mixed with the first additive portion. The mixing may take place directly after the HTST and filtration operations, but it is also possible to keep the portions separate until use of the medium for cell cultivation. Sterility of the medium is suitably ensured by filtration through a sterilization grade filter commonly known in the art. The sterile filtration can be performed on the mixed medium or on the portions separately.

In a second aspect, the invention discloses a method of cultivating cells. This method comprises the steps of the viral clearance/inactivation methods disclosed above, and further the steps of:

Transferring the cell culture medium to a bioreactor (vi). The bioreactor can be of any size, e.g. a shake bottle or spinner bottle for small scale cultivation, a rocking bag single use bioreactor (e.g. WAVE™ from GE Healthcare Life Sciences, USA) for medium scale and a stirred bag (e.g. Xcellerex™ XDR from GE Healthcare Life Sciences, USA) or stainless steel stirred tank bioreactor for larger scales. The cell culture medium is suitably sterilized by passage through a sterilization grade filter, as discussed above, before or during transfer to the bioreactor.

Transferring cells to the bioreactor (vii). The cells can be e.g. animal cells, such as mammalian cells, or microbial cells, e.g. bacterial cells and the cell culture medium composition is suitably selected to fit the particular cell type and cultivation conditions used.

Cultivating the cells in the cell culture medium in the bioreactor (viii). During this step, the cell culture medium is kept at a suitable temperature and agitated, while gases are passed into and out of the bioreactor and cell culture medium and/or culture medium components may be added to the bioreactor.

EXAMPLES

Example 1

10 L bulk medium with the composition according to Table 1 is prepared. All ingredients are of a grade suitable for cell culture.

TABLE 1

| Bulk medium (aqueous solution) | | | | |
|---|---|---|---|---|
| | Component | Mw (g/mol) | Conc. (mg/L) | Conc. (mmol/L) |
| Amino acids | L-Arginine HCl | 210.65 | 84 | 0.399 |
| | L-Cysteine 2HCl | 313.11 | 62.57 | 0.20 |
| | L-Glutamine | 146.10 | 584 | 3.997 |
| | Glycine | 75.10 | 30 | 0.399 |
| | L-Histidine HCl, H2O | 209.65 | 42 | 0.200 |
| | L-Isoleucine | 131.20 | 105 | 0.800 |
| | L-Leucine | 131.20 | 105 | 0.800 |
| | L-Lysine HCl | 182.65 | 146 | 0.799 |
| | L-Methionine | 149.20 | 30 | 0.201 |
| | L-Phenylalanine | 165.20 | 66 | 0.400 |
| | L-Serine | 105.10 | 42 | 0.400 |
| | L-Threonine | 119.10 | 95 | 0.798 |
| | L-Tryptophan | 204.20 | 16 | 0.04 |
| | L-Tyrosine 2Na, 2H2O | 261.20 | 103.79 | 0.397 |
| | L-Valine | 117.10 | 94 | 0.803 |
| Sugar | D-Glucose | 180.00 | 4500 | 25 |
| Salts, buffers | Magnesium sulfate anhydrous | 120.40 | 97.67 | 0.8112 |
| | Potassium chloride | 74.55 | 400 | 5.3655 |
| | Sodium phosphate dibasic H2O | 142.00 | 125 | 0.7813 |
| | Sodium chloride | 58.44 | 6650 | 113.9 |
| | Calcium chloride anhydrous | 111.00 | 200 | 1.802 |
| | Sodium bicarbonate | 84.01 | 3700 | 44.04 |
| Trace minerals | Ferric nitrate 9H2O | 101.10 | 0.10 | 0.0010 |
| Others | Phenol red | | 15 | |

400 mL of an additive solution with the composition according to Table 2 is further prepared. All ingredients are of a grade suitable for cell culture.

TABLE 2

| Additive solution (aqueous solution) | | | | |
|---|---|---|---|---|
| | Component | Mw (g/mol) | Conc. (mg/L) | Conc. (mmol/L) |
| Vitamins, minute organics | Choline chloride | 140.00 | 100 | 0.714 |
| | Folic acid | 441.0 | 100 | 0.227 |
| | I-inositol | 180.00 | 200 | 1.111 |
| | Niacinamide | 122.00 | 100 | 0.820 |
| | D-Calcium pantothenate | 477.0 | 100 | 0.210 |
| | Pyridoxal hydrochloride | 204.00 | 100 | 0.490 |
| | Riboflavin | 376.0 | 10.0 | 0.0266 |
| | Thiamine hydrochloride | 337.0 | 100 | 0.297 |

The bulk medium is heat treated (HTST) in a lab setup with a peristaltic pump conveying the liquid through a coil of 2.5 mm i.d. stainless steel tubing immersed in a 100° C. oil bath and further into a coil of 2.5 mm i.d. stainless steel tubing immersed in a 20° C. water bath. The lengths of the coils are: 100° C. oil bath—4 m and 20° C. water bath—2 m. With a volumetric flow rate of 60 mL/min, the residence times in the coils will then be oil bath—20 s and water bath—10 s, approximately corresponding to a heating time of 10 s, a hold time at 100° C. of 10 s and a cooling time of 10 s. After passage of the water bath, the medium is collected in a flexible plastic bag.

The additive solution is passed through an Asahi Kasei Planova 20N virus filter cartridge and collected in a flexible plastic bag.

The bulk medium and additive solution are mixed and conveyed via a sterilization filter into a 10 L working volume Cellbag (GE Healthcare Life Sciences), mounted on a WAVE 25 rocking bioreactor support. The Cellbag is seeded with CHO cells, which are cultivated under the following conditions: Temp 36.8+/−0.2° C., pH 7.00+/−0.05 (controlled with $CO_2$, $NaHCO_3$), dissolved oxygen 60+/−2% of air saturation (controlled with oxygen enriched air on demand).

Example 2

As Example 1, but the bulk medium is divided into two solutions of equal volume; one containing only glucose and water and the other containing all the other components. After separate HTST of the two solutions, they are mixed and used as in Example 1. This reduces the risk of heat-induced Maillard reactions between the amino acids and the glucose.

Example 3

As Example 2, but the magnesium sulfate, calcium chloride and ferric nitrate are contained in the glucose solution. This reduces any potential risk of phosphate precipitation during the HTST.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. All patents and patent applications mentioned in the text are hereby incorporated by reference in their entireties as if individually incorporated.

What is claimed is:

1. A method for virus clearance of a cell culture medium, comprising the steps of:
   i) providing a bulk medium portion, comprising amino acids and glucose;
   ii) providing a first additive portion, comprising vitamins in aqueous solution;
   iii) subjecting the bulk medium portion to a high temperature short time treatment (HTST);
   iv) passing the first additive portion through a virus retentive ultrafilter, wherein or the virus retentive ultrafilter has a molecular weight (Mw) cut-off value below 100 kDa; and
   v) after steps iii) and iv), mixing the bulk medium portion with the first additive portion to obtain a cell culture medium cleared from viruses.

2. The method of claim 1, wherein step iii) comprises heating the bulk medium portion to a temperature of about 85-110° C., maintaining said temperature for about 1 s to about 10 min, and cooling the bulk medium portion to <40° C.

3. The method of claim 2, wherein in step iii) the rate of heating is at least 5° C. per s.

4. The method of claim 2, wherein in step iii) the rate of cooling is at least 5° C. per s.

5. The method of claim 2, wherein the heating is performed in a flow-through heater.

6. The method of claim 5, wherein the flow-through heater is an inductive heater.

7. The method of claim 2, wherein the cooling is performed in a flow-through cooler.

8. The method of claim 1, wherein the first additive portion comprises thiamine and/or pantothenic acid.

9. The method of claim 1, wherein the bulk medium portion is passed through a sterilization-grade filter after step iii) and before step v).

10. The method of claim 1, wherein after step v), the cell culture medium is passed through a sterilization-grade filter.

11. The method of claim 1, further comprising the steps of:
   providing a second additive portion, comprising one or more proteinaceous components;
   subjecting the second additive portion to gamma or electron beam radiation; and
   mixing the irradiated second additive portion with the bulk medium portion and the first additive portion to obtain a cell culture medium.

12. The method of claim 11, wherein the proteinaceous components comprise serum.

13. The method of claim 11, wherein the proteinaceous components comprise a protein hydrolysate.

14. A method of cultivating cells, comprising the steps as set forth in claim 1 and further comprising the steps of:
   transferring the cell culture medium cleared from viruses to a bioreactor;
   transferring cells to the bioreactor; and
   cultivating the cells in the cell culture medium in the bioreactor.

15. The method of claim 14, wherein the cells are animal cells.

16. The method of claim 14, wherein the cells are microbial cells.

17. A method for virus clearance of a cell culture medium, comprising the steps of:
   i) providing an amino acid portion, comprising amino acids, and a sugar portion, comprising glucose;
   ii) providing a first additive portion, comprising vitamins in aqueous solution;
   iii) subjecting the amino acid and sugar portions to a high temperature short time treatment (HTST);
   iv) passing the first additive portion through a virus retentive ultrafilter, wherein the virus retentive ultrafilter has a molecular weight (Mw) cut-off value below 100 kDa; and
   v) after steps iii) and iv), mixing the amino acid and sugar portions with the first additive portion to obtain a cell culture medium cleared from viruses.

18. The method of claim 17, wherein step iii) comprises separately heating the amino acid and sugar portions to a temperature of about 85-110° C., maintaining said temperature for about 1 s to about 10 min, and cooling the amino acid and sugar portions to <40° C.

19. The method of claim 17, wherein the first additive portion comprises thiamine and/or pantothenic acid.

20. The method of claim 18, wherein the heating is performed in a flow-through heater and the cooling is performed in a flow-through cooler.

* * * * *